United States Patent
Imai et al.

(10) Patent No.: US 10,286,204 B2
(45) Date of Patent: May 14, 2019

(54) CLAMP AND BLOOD BAG SYSTEM

(71) Applicant: TERUMO KABUSHIKI KAISHA, Shibuya-ku, Tokyo (JP)

(72) Inventors: Tadashi Imai, Shizuoka (JP); Masanori Sato, Trivandrum (IN)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 15/621,668

(22) Filed: Jun. 13, 2017

(65) Prior Publication Data

US 2017/0281923 A1 Oct. 5, 2017

Related U.S. Application Data

(63) Continuation of application No. 14/081,815, filed on Nov. 15, 2013, now abandoned, which is a (Continued)

(30) Foreign Application Priority Data

May 16, 2011 (JP) ................. 2011-109025

(51) Int. Cl.
- *A61M 39/28* (2006.01)
- *F16K 7/06* (2006.01)
- *A61M 5/14* (2006.01)

(52) U.S. Cl.
CPC ........ *A61M 39/284* (2013.01); *A61M 5/1407* (2013.01); *F16K 7/063* (2013.01); *Y10T 29/49405* (2015.01)

(58) Field of Classification Search
CPC .. A61M 39/22; A61M 39/284; A61M 5/1407; A61M 39/28; F16K 7/04; F16K 7/06; F16K 7/063; Y10T 29/49405
(Continued)

(56) References Cited

U.S. PATENT DOCUMENTS 350,850 A 10/1886 Tatum
2,722,932 A 11/1955 Hickey
(Continued)

FOREIGN PATENT DOCUMENTS

EP 1 000 633 A2 5/2000
FR 2 590 645 A1 5/1987
(Continued)

OTHER PUBLICATIONS

International Search Report (PCT/ISA/210) dated May 22, 2012, by the Japanese Patent Office as the International Searchng Authority for International Application No. PCT/JP2012/058922.
(Continued)

*Primary Examiner* — Robert K Arundale
*Assistant Examiner* — Jonathan J Waddy
(74) *Attorney, Agent, or Firm* — Buchanan Ingersoll & Rooney PC

(57) ABSTRACT

A blood bag system includes a clamp installed in a flexible first tube. The clamp includes: a base section having a protrusion section, an opening/closing section having a pressing protrusion section that presses a side surface of the first tube, and a bent section that connects the base section and opening/closing section. The base section is provided with a pair of cutout sections opened to a side surface where the first tube can be inserted by interposing the protrusion section. The clamp is configured such that a portion of the first tube where the clamp is installed is bent while the clamp is released.

19 Claims, 10 Drawing Sheets

Related U.S. Application Data continuation of application No. PCT/JP2012/058922, filed on Apr. 2, 2012.

(58) Field of Classification Search
USPC .................................................. 251/4, 9, 10
See application file for complete search history.

(56) References Cited

U.S. PATENT DOCUMENTS

| | | | |
|---|---|---|---|
| 3,419,245 | A | 12/1968 | Scola |
| 3,822,052 | A | 7/1974 | Lange |
| 3,942,228 | A | 3/1976 | Buckman et al. |
| 4,235,412 | A | 11/1980 | Rath et al. |
| 4,588,160 | A | 5/1986 | Flynn et al. |
| 5,180,504 | A | 1/1993 | Johnson et al. |
| 5,203,056 | A | 4/1993 | Funk |
| 6,113,062 | A | 9/2000 | Schnell et al. |
| 6,234,448 | B1 | 5/2001 | Porat |
| 7,686,279 | B2 | 3/2010 | Merbonne |
| 8,262,639 | B2 | 9/2012 | Mathias |
| 2002/0087126 | A1 | 7/2002 | Quah |
| 2003/0135157 | A1 | 7/2003 | Saulenas et al. |
| 2006/0081797 | A1 | 4/2006 | Zerfas |
| 2008/0082079 | A1 | 4/2008 | Braga |
| 2010/0152681 | A1* | 6/2010 | Mathias ............ A61M 39/284 604/250 |

FOREIGN PATENT DOCUMENTS

| | | |
|---|---|---|
| JP | 2-004384 A | 1/1990 |
| JP | 2-68851 U | 5/1990 |
| JP | 2-123243 U | 10/1990 |
| JP | 2003-339862 A | 12/2003 |
| JP | 2004-249110 A | 9/2004 |
| JP | 3971654 B2 | 9/2007 |
| JP | 2008-220425 A | 9/2008 |
| WO | WO 03/063945 A1 | 8/2003 |

OTHER PUBLICATIONS

Excerpt of an Office Action dated Feb. 13, 2015, by the Chinese Patent Office in corresponding Chinese Patent Application No. 201280023495.9. (1 page).

Extended European Search Report dated Nov. 19, 2014, by the European Patent Office in corresponding European Application No. 12786745.5-1662. (8 pages).

\* cited by examiner

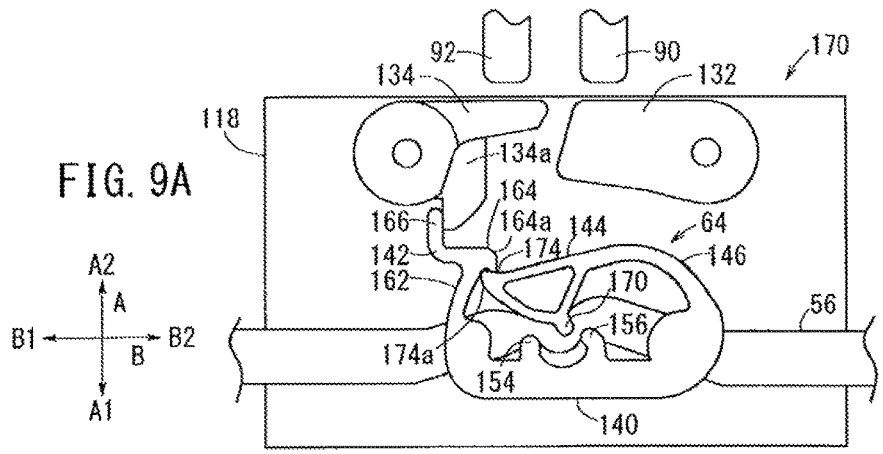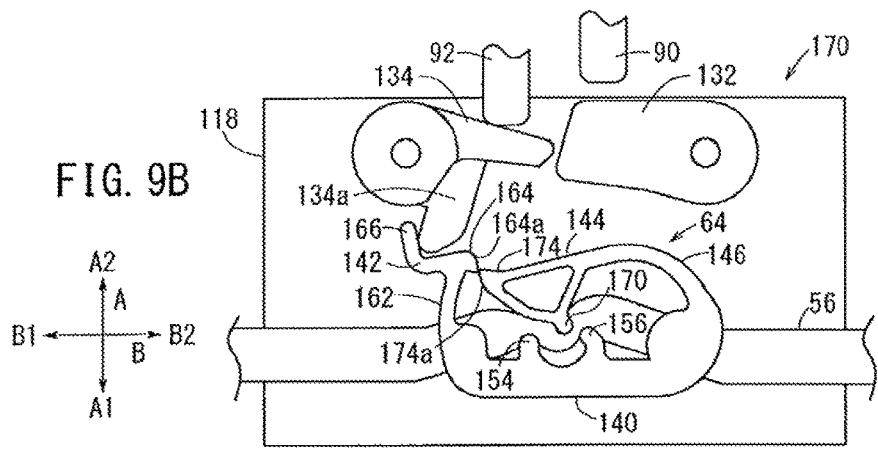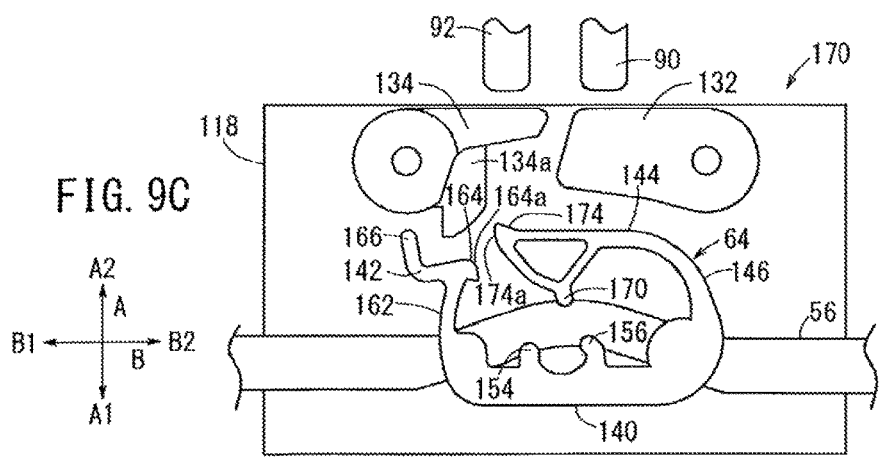

CLAMP AND BLOOD BAG SYSTEM

CROSS REFERENCES TO RELATED APPLICATIONS

This application is a continuation U.S. patent application Ser. No. 14/081,815 filed on Nov. 15, 2013, which is a continuation of International Application No. PCT/JP2012/058922 filed on Apr. 2, 2012, and which claims priority to Japanese Application No. 2011-109025 filed on May 16, 2011, the entire contents of which are incorporated herein by reference.

TECHNICAL FIELD

The present invention generally relates to a clamp which closes and opens a flow path in a flexible tube and to a blood bag system having the clamp.

BACKGROUND DISCUSSION

In the past, whole blood transfusion was the mainstream of the blood transfusion technology, in which all the components of blood obtained by blood donation are transfused. Recently, as technologies have advanced, blood component transfusion is performed, in which the obtained blood is separated into components such as red blood cells, platelets, and plasma, and only the component necessary for a patient are transfused. The blood component transfusion makes it possible to reduce burdens or side effects on a patient's circulatory system and effectively use the donated blood.

The blood (whole blood) obtained by blood donation or a blood component prepared from the whole blood is separated through centrifugation into a plurality of layers. For instance, by centrifuging whole blood, the whole blood is separated into a light supernatant PPP (platelet poor plasma) fraction, a heavy precipitated CRC (concentrated red blood cells) fraction, and a buffy coat formed therebetween. By centrifuging the buffy coat, the buffy coat is separated into a supernatant component that contains platelets and leukocytes and a precipitated component that contains red blood cells. When the residual component remaining after removal of leukocytes and platelets from whole blood is centrifuged, the component is separated into a plasma layer which is the supernatant component and a red blood cell layer which is the precipitated component.

In order to separate whole blood into a plurality of blood components and put and preserve the blood components in a plurality of preservation bags, or in order to further separate a blood component prepared from whole blood into a plurality of blood components and put and preserve the blood components in a plurality of preservation bags, a blood bag system in which a plurality of bags are connected using a plurality of tubes has been used. In addition, in such a blood bag system, in order to perform a predetermined blood treatment by switching the communication state between the bags, a clamp is provided for closing and opening the flow path in the tube.

Known clamps extend in a substantially annular shape from one end to the other end, and the tube is inserted into a pair of facing through-holes in a substantially straight state. In this state, the flow path of the tube is closed by clamping the clamp and pressing the side surface of the tube with a pair of protrusion sections. An example of this clamp is described in Japanese Patent Publication No. 3971654.

In the aforementioned clamp, it is necessary to insert the tube into a pair of through-holes. For this reason, for example, it is necessary to insert the tube into a pair of the through-holes of the clamp in the course of manufacturing a blood bag system before a blood bag, a branching connector, and the like are connected to both ends of the tube. This work consumes time.

Since the tube has a substantially straight state while it is inserted into a pair of the through-holes, the clamp may easily move with respect to the tube before the flow path of the tube is closed. In particular, for example, when the tube is arranged to extend in a vertical direction, the clamp may move downward due to gravity, which may affect workability of blood treatment.

SUMMARY

One aspect disclosed here involves a clamp that closes a flow path of a flexible tube when the clamp is in a closed position and opens the flow path of the flexible tube when the clamp is in a released position. The clamp comprises: a base section having a first protrusion section that makes contact with a side surface of the tube; an opening/closing section having a second protrusion section that closes the flow path of the tube by pressing the side surface of the tube toward the first protrusion section; and an intermediate section connecting the base section and the opening/closing section. The base section includes a pair of cutout sections through which the tube is to pass, with the first protrusion section being interposed between the pair of cutout sections. Each of the cutout sections opens to a side surface located perpendicularly to an arrangement direction in which the pair of cutout sections are arranged, and the first protrusion section and the pair of cutout sections are configured such that a portion of the tube passing through the clamp when the clamp is installed on the tube is bent when the clamp is in the released position.

According to another aspect, a clamp is positionable along a length of a flexible tube to close a flow path of the flexible tube when the clamp is in a closed position and to open the flow path of the flexible tube when the clamp is in a released position. The clamp comprises: a base section possessing a bottom surface and an inner surface facing in opposite directions, with the base section also possessing side surfaces which intersect and extend away from the bottom surface, and with the base section including a first protrusion projecting away from the inner surface to make contact with a side surface of the tube when the clamp is mounted on the tube; an opening/closing section positioned in spaced apart and opposing relation to the base section so that a space exists between the opening/closing section and the base section, with the opening/closing section including a second protrusion that projects toward the inner surface of the base section, and with the second protrusion being positioned to make contact with the flexible tube without closing the flow path of the tube when the clamp is in the released position and to make contact with the flexible tube and press the flexible tube toward the first protrusion to close off the flow path in the flexible tube when the clamp is in the closed position; and an intermediate section connecting the base section and the opening/closing section in a manner permitting the opening/closing section to move toward the base section when the clamp is in the released position. The base section includes first and second cutout sections through which the tube passes when the clamp is mounted on the tube, wherein the first protrusion is positioned between the first and second cutout sections so that the first cutout section, the first protrusion and the second cutout section are arranged in such order in an arrangement direction which is perpendicular to the side surfaces of the base section. Each of the cutout sections opens to a common one of the side surfaces of the base section, and the first protrusion and the first and second cutout sections are configured such that a portion of the tube passing through the clamp when the clamp is positioned along the tube is bent when the clamp is in the released position.

Since the cutout sections open to the side surface of the base section located perpendicularly to an arrangement direction of a pair of the cutout sections, it is possible to install the clamp in the tube even after a predetermined member is connected to the both ends of the tube. As a result, it is possible to relatively easily replace the clamp with a new one even when a problem occurs in the clamp after the clamp is installed in the tube. In addition, the first protrusion section and a pair of the cutout sections are configured such that a portion making contact with the first protrusion section in the tube is bent while the clamp is released. As a result, the tube is pressed against wall surfaces of each cutout section by virtue of a restoring force (elastic force) of the tube. Therefore, it is possible to prevent the clamp from easily moving with respect to the tube before the flow path of the tube is closed.

In the clamp described above, each of the cutout sections may include holding holes for holding the tube by penetrating an outer surface and an inner surface of the base section, and a holding surface located in the opening/closing section side out of wall surfaces of the holding holes of at least one of the cutout sections may be located in a bottom surface side of the base section relative to a position displaced from a leading end of the first protrusion section toward the opening/closing section side by an outer diameter length of the tube.

Because the holding surface of at least one cutout section is located in the bottom surface side of the base section relative to the position displaced from the leading end of the first protrusion section toward the opening/closing section side by the outer diameter length of the tube, it is possible to securely bend a portion of the tube where the clamp is installed while the clamp is released.

In the clamp described above, the holding surfaces of at least one of the cutout sections may be located in the second protrusion section side relative to the first protrusion section. It is thus possible to bend the tube at an obtuse angle before the fluid path of the tube is closed. Accordingly, it is possible to prevent the flow path of the tube from being closed while the clamp is installed in the tube.

The clamp is preferably configured so that the holding surface of at least one of the cutout sections is inclined to the opening/closing section side along the inner surface of the base section. This helps make it possible to increase a contact area between the side surface and the holding surface of the tube. Therefore, it is possible to further prevent movement of the clamp with respect to the tube.

The base section may be provided with a third protrusion section that is located between the one cutout section and the first protrusion section and makes contact with a side surface of the tube. Because the portion making contact with the first and third protrusion sections in the tube is bent, it is possible to further suppress the tube from being excessively bent and stably hold the tube.

Each of the cutout sections may be formed in a substantially L-shape as seen in a plan view and may open to a bottom surface of the base section. With each cutout section formed in a substantially L-shape, it is possible to make difficult to detach the tube from a pair of the cutout sections. In addition, because the cutout section is opened to the side surface and the bottom surface of the base section, it is possible to insert the tube in the cutout section while a predetermined member is connected to both ends thereof.

According to another aspect, there is provided a blood bag system including: a plurality of bags configured to contain whole blood or a blood component; at least one tube that connects the plurality of bags; and the aforementioned clamp installed along the tube.

In the blood bag system described above, it is possible to install the clamp in the tube after a plurality of the bags are connected to the tube. Therefore, it is possible to simplify manufacturing of the blood bag system. In addition, the clamp does not easily move with respect to the tube before the clamp closes the flow path of the tube. Therefore, it is possible to rather easily perform the clamping/unclamping manipulation of the clamp at a defined position in the tube.

It is possible to install the clamp in the tube even after a predetermined member is connected to the both ends of the tube. In addition, it is possible to suppress the clamp from easily moving with respect to the tube before the flow path of the tube is closed.

With the blood bag system and clamp disclosed here, it is possible to install the clamp in the tube after a plurality of the bags are connected to the tube. Therefore, it is possible to simplify manufacturing of the blood bag system. In addition, since the clamp does not easily move with respect to the tube before the clamp closes the flow path of the tube, it is possible to perform the clamping/unclamping manipulation of the clamp at a predetermined position in the tube.

According to another aspect, a method comprises: mounting a clamp on a flexible tube which possesses one end connected to a first bag and an opposite end connected to a second bag, with the first and second bags each possessing an interior that receives blood or a blood component. The clamp comprises: a base section possessing a bottom surface and a side surface intersecting the bottom surface, with the base section including a projecting first protrusion; an opening/closing section positioned in opposing spaced apart relation to the base section so that a space exists between the opening/closing section and the base section, with the opening/closing section including a projecting second protrusion that projects toward the base section, and with the first protrusion projecting towards the opening/closing section; and an intermediate section connecting the base section and the opening/closing section in a manner permitting the opening/closing section to move toward the base section. The base section includes first and second cutout sections, with the first protrusion positioned between the first and second cutout sections, and each of the cutout sections opens to the side surface of the base section by way of respective lateral through-holes. The clamp is mounted on the tube at a position between the first bag connected to the one end of the tube and the second bag connected to the other end of the tube by passing a portion of the tube through the lateral through-holes in the side surface and introducing the portion of the tube into the space between the base section and the opening/closing section.

According to another aspect, a clamp positionable along a length of a flexible tube to close a flow path of the flexible tube when the clamp is in a closed position and to open the flow path of the flexible tube when the clamp is in a released position, comprising: a base section possessing a bottom surface and an inner surface facing opposite directions, the base section also possessing side surfaces which intersect and extend away from the bottom surface, the base section including a first protrusion projecting from the inner surface to make contact with a side surface of the tube when the clamp is mounted on the tube; an opening/closing section positioned in spaced apart and opposing relation to the base section so that a space exists between the opening/closing section and the base section, the opening/closing section including a second protrusion that projects toward the inner surface of the base section, the second protrusion being positioned to make contact with the flexible tube without closing the flow path of the tube when the clamp is in the released position and to make contact with the flexible tube and press the flexible tube toward the first protrusion to close off the flow path in the flexible tube when the clamp is in the closed position; an intermediate section connecting the base section and the opening/closing section in a manner permitting the opening/closing section to move toward the base section when the clamp is in the released position; the base section including first and second cutout sections through which the tube passes when the clamp is mounted on the tube, the first protrusion being positioned between the first and second cutout sections so that the first cutout section, the first protrusion and the second cutout section are arranged in order in an arrangement direction which is perpendicular to the side surfaces of the base section, the arrangement direction being an extending direction (X) of the base section; the first protrusion and the first and second cutout sections being configured such that a portion of the tube passing through the clamp when the clamp is positioned along the tube is bent when the clamp is in the released position, wherein the side surface of the tube contacts the first protrusion section between the first and second cutout sections; and each of the first and second cutout sections being opened to one of the side surfaces of the base section located perpendicularly to the arrangement direction of the pair of the cutout sections of the base section, and is formed in a substantially L-shape as seen in a plan view, wherein the first cutout section is at one end of the base section in the arrangement direction and the second cutout section is at an opposite end of the base section in the arrangement direction, and wherein a positional relationship of the first cutout section, the second cutout section, the first protrusion, and the second protrusion is such that the tube has an entry-to-exit angle between 110° and 150°.

According to a further aspect, A clamp that closes a flow path of a flexible tube when the clamp is in a closed position and opens the flow path of the flexible tube when the clamp is in a released position, comprising: a base section having a first protrusion section that makes contact with a side surface of the tube; an opening/closing section having a second protrusion section that closes the flow path of the tube by pressing the side surface of the tube toward the first protrusion section; an intermediate section connecting the base section and the opening/closing section; the base section including a pair of cutout sections through which the tube is to pass, the first protrusion section being interposed between the pair of cutout sections; the first protrusion section and the pair of cutout sections being configured such that a portion of the tube passing through the clamp when the clamp is installed on the tube is bent when the clamp is in the released position, wherein the side surface of the tube contacts the first protrusion section between the pair of cutout sections; and wherein each of the pair of cutout sections is opened to a side surface located perpendicularly to an arrangement direction of the pair of cutout sections of the base section, which is an extending direction (X) of the base section, and is formed in a substantially L-shaped as seen in a plan view, wherein each of the cutout sections comprises: a holding hole that holds the tube, each of the holding holes penetrating an outer surface and an inner surface of the base section; a holding surface is located in an opening/closing section side of the holding hole of at least one of the cutout sections, the holding surface being located in a bottom surface side of the base section relative to a position displaced from a leading end of the first protrusion section toward the opening/closing section side by an outer diameter length of the tube; and wherein a positional relationship of each of the holding holes, the first protrusion, and the second protrusion is such that the tube has an entry-to-exit angle between 110° and 150°.

According to another aspect, a clamp positionable along a length of a flexible tube to close a flow path of the flexible tube when the clamp is in a closed position and to open the flow path of the flexible tube when the clamp is in a released position, comprising: a base section possessing a bottom surface and an inner surface facing opposite directions, the base section also possessing side surfaces which intersect and extend away from the bottom surface, the base section including a first protrusion projecting from the inner surface to make contact with a side surface of the tube when the clamp is mounted on the tube; an opening/closing section positioned in spaced apart and opposing relation to the base section so that a space exists between the opening/closing section and the base section, the opening/closing section including a second protrusion that projects toward the inner surface of the base section, the second protrusion being positioned to make contact with the flexible tube without closing the flow path of the tube when the clamp is in the released position and to make contact with the flexible tube and press the flexible tube toward the first protrusion to close off the flow path in the flexible tube when the clamp is in the closed position; an intermediate section connecting the base section and the opening/closing section in a manner permitting the opening/closing section to move toward the base section when the clamp is in the released position; the base section including first and second cutout sections through which the tube passes when the clamp is mounted on the tube, the first protrusion being positioned between the first and second cutout sections so that the first cutout section, the first protrusion and the second cutout section are arranged in order in an arrangement direction which is perpendicular to the side surfaces of the base section, the arrangement direction being an extending direction (X) of the base section; the first protrusion and the first and second cutout sections being configured such that a portion of the tube passing through the clamp when the clamp is positioned along the tube is bent when the clamp is in the released position, wherein the side surface of the tube contacts the first protrusion section between the first and second cutout sections; and each of the first and second cutout sections being opened to one of the side surfaces of the base section located perpendicularly to the arrangement direction of the pair of the cutout sections of the base section, and is formed in a substantially L-shape as seen in a plan view, and wherein the first and second cutout sections each have an opening on a planar portion of a bottom surface of the base section and the openings of the first and second cutout sections are at ends of the first and second cutout sections that are bottom-most ends, and which are opposite from a holding surface, the holding surface being located in a bottom surface side of the base section relative to a position displaced from a leading end of the first protrusion section toward the opening/closing section side by an outer diameter length of the tube, and wherein a positional relationship of the first cutout section, the second cutout section, the first protrusion, and the second protrusion is such that the tube is configured to extend about an entry axis.

BRIEF DESCRIPTION OF THE DRAWINGS

FIG. 9A is a diagram illustrating a condition that the first tube is closed by clamping the clamp.

FIG. 9B is a diagram illustrating a condition that engagement of an engagement claw is released.

FIG. 9C is a diagram illustrating a condition that the clamp is released by releasing the engagement claw.

DETAILED DESCRIPTION

Set forth below with reference to the accompanying drawings is a detailed description of a clamp and a blood bag system representing an example of the clamp and a blood bag system disclosed here.

Figure 1:
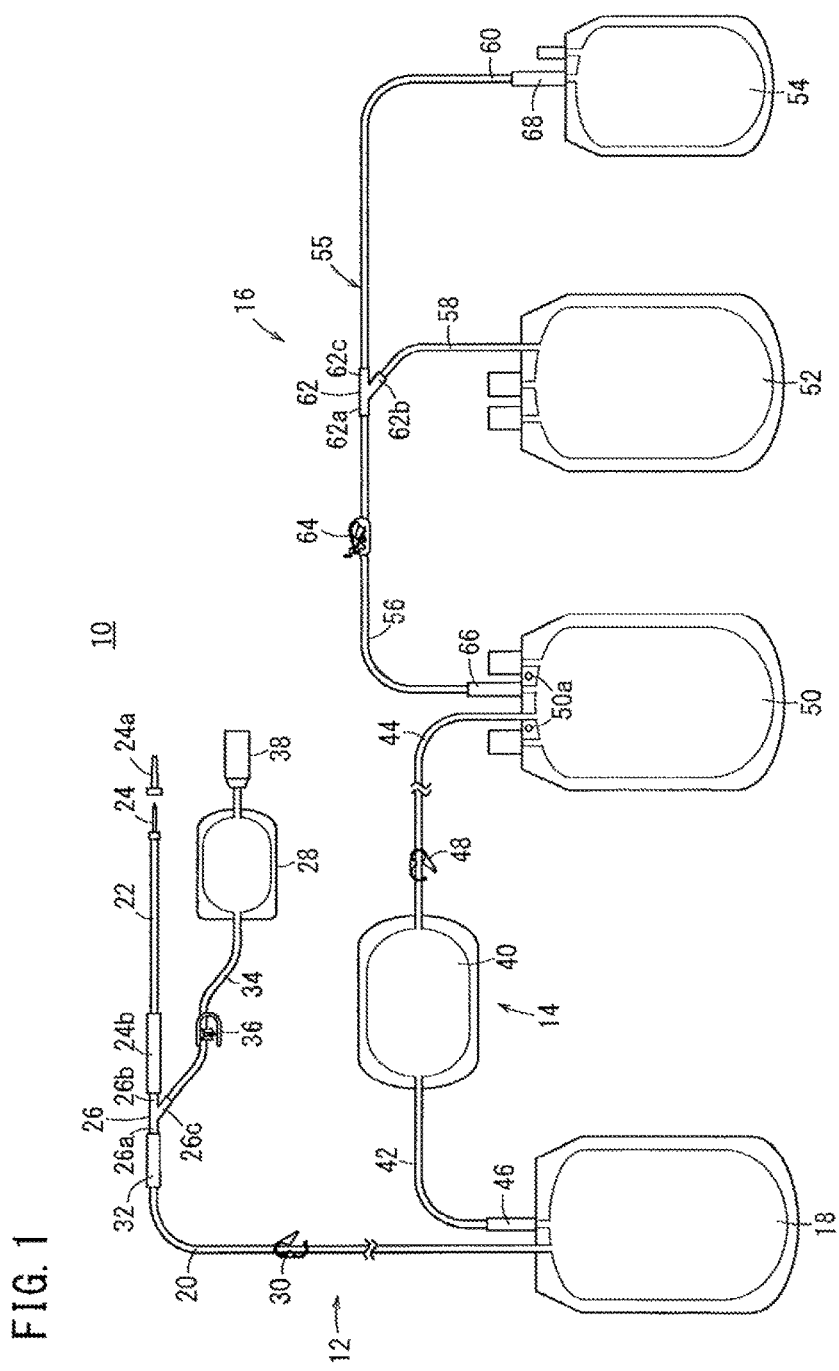
FIG. 1 is a plan view illustrating a blood bag system according to an embodiment disclosed by way of example here.

Referring to FIG. 1, the blood bag system 10 centrifuges blood containing a plurality of components into a plurality of components having a different specific gravity (for example, three components including a relatively low specific gravity component, an intermediate specific gravity component, and a relatively high specific gravity component, or two components including a relatively low specific gravity component and a relatively high specific gravity component) and puts and preserves the components separately in different bags. The blood bag system 10 according to the embodiment is configured to centrifuge a residual blood component obtained by removing leukocytes and platelets from whole blood into two components including plasma and concentrated red blood cells and put and preserve the plasma and the concentrated red blood cells separately in different bags.

The blood bag system 10 includes a blood collection unit 12 that collects blood (whole blood) from a donor, a pre-treatment unit 14 that removes a predetermined blood component from the whole blood, and a separator unit 16 that centrifuges the residual blood component obtained by removing the predetermined component into a plurality of blood components and puts (preserves) the blood components in different bags.

The blood collection unit 12 will first be described. The blood collection unit 12 includes a blood collection bag 18, first and second blood collection tubes 20 and 22, a blood collection needle 24, a branching connector 26, and an initial flow collecting bag 28.

The blood collection bag 18 is a bag that contains (preserves) blood (whole blood) collected from the donor. Preferably, an anticoagulant is placed in the blood collection bag 18 in advance. The anticoagulant is typically a liquid and may include, for example, an acid citrate dextrose formula-A (ACD-A) solution, a citrate phosphate dextrose (CPD) solution, a citrate phosphate dextrose adenine (CPDA-1) solution, a heparin sodium solution, and the like. The amount of the anticoagulant is appropriately set depending on the amount of blood to be collected.

The blood collection bag 18 is configured in a bag shape by overlapping flexible sheet materials made of a flexible resin such as polyvinyl chloride or polyolefin on each other and welding or adhering (through thermal fusion bonding or high-frequency fusion bonding) peripheral sealing portions of the sheet materials to each other. Similarly, the initial flow collecting bag 28 is also configured in a bag shape.

One end of the first blood collection tube 20 (proximal-side blood collection tube) is connected to an upper portion of the blood collection bag 18. A clamp 30 for closing or opening a flow path in the first blood collection tube 20 is provided at an intermediate portion of the first blood collection tube 20. This clamp 30 is a resin member possessing an overall flat C-shape. The clamp 30 includes a pair of pressing sections which press the side surfaces of the first blood collection tube 20 and an engagement section that can engage or disengage ends of the C-shape to/from each other, so that the flow path of the first blood collection tube 20 is closed by engaging both ends to each other and pressing the first blood collection tube 20 by the pair of pressing sections.

One end of a frangible part (breakable communication member) 32 is connected to the other end of the first blood collection tube 20. The frangible part 32 is configured such that the flow path is closed in an initial state and is then opened by performing a breaking manipulation.

Such a frangible part 32 includes a tube formed of a flexible resin such as polyvinyl chloride and a tubular body that is connected to the inside of the tube in a liquid-tight manner and has a closed end and a brittle portion formed in a part of the longitudinal direction. In order to open the frangible part 32, the tubular body is bent by a finger or the like from the outside of the tube to break the brittle portion. As a result, the flow path in the tube closed by the tubular body is opened, and the frangible part 32 is opened.

A first port 26a of the branching connector 26 is connected to the other end of the frangible part 32. One end of the second blood collection tube (distal-side blood collection tube) 22 is connected to a second port 26b of the branching connector 26, and the blood collection needle 24 is connected to the other end of the second blood collection tube 22. A cap 24a is installed in the blood collection needle 24 before use, and a needle guard 24b is installed in the blood collection needle 24 after use. The needle guard 24b is arranged movably along the longitudinal direction of the second blood collection tube 22.

One end of a branching tube 34 is connected to a third port 26c of the branching connector 26. A clamp 36 that closes or opens a flow path of the branching tube 34 is located at the intermediate portion of the branching tube 34. It is difficult to open to the clamp 36 once it is clamped. The clamp disclosed in Japanese Patent Publication No. 05-23792 B2 is an example of the clamp 36 which can be employed.

The initial flow collecting bag 28 is connected to the other end of the branching tube 34. In order to collect blood from a donor, first, a predetermined amount of the initial flow of the collected blood (initial flow of blood collection) is put in or introduced into the initial flow collecting bag 28 before the blood is put in or introduced into the blood collection bag 18. In this case, the clamp 36 is in an opened state while the frangible part 32 is kept in a closed state (initial state). As a result, it is possible to prevent the initial flow of blood collection from being introduced into the first blood collection tube 20 side, that is, to the blood collection bag 18 side. Instead, the initial flow of blood collection is introduced into the initial flow collecting bag 28 through the second blood collection tube 22, the branching connector 26, and the branching tube 34.

A sampling port 38 is connected to the initial flow collecting bag 28, and a blood collection tube is installed in the sampling port 38, so that the initial flow of blood collection is collected in the blood collection tube. The initial flow of blood collection is provided for a test. In addition, the parts from the branching connector 26 to the sampling port 38 may be omitted depending on utilization.

The pretreatment unit 14 includes a filter 40 that removes predetermined cells, an inlet-side tube 42 having one end connected to the blood collection bag 18 and other end connected to an inlet of the filter 40, and an outlet-side tube 44 having one end connected to an outlet of the filter 40 and the other end connected to the separator unit 16.

In this embodiment, the filter 40 is configured as a leukocyte-removing filter. Such a leukocyte-removing filter may be structured such that a liquid-passing porous body having a plurality of micropores communicating from one side surface to the other side surface is housed in a pouch-like housing formed of resin. In this embodiment, the filter 40 is capable of supplementing platelets as well.

The inlet-side tube 42 is a tube for delivering the blood collected from a donor from the blood collection bag 18 to the filter 40. The inlet-side tube 42 is connected to an upper portion of the blood collection bag 18. In this embodiment, a frangible part 46 is provided in an end of the inlet-side tube 42 in the blood collection bag 18 side. The frangible part 46 has the same configuration and functionality as those of the frangible part 32 described above.

The outlet-side tube 44 is a tube for delivering the residual blood components (in this embodiment, leukocytes and platelets) obtained by removing predetermined cells using the filter 40 to the separator unit 16 (specifically, a primary bag 50 described below). A clamp 48 that closes and opens a flow path of the outlet-side tube 44 is provided in the middle of the outlet-side tube 44. The clamp 30 described above may be employed as the clamp 48.

Next, the separator unit 16 will be described. The separator unit 16 includes a primary bag (first bag) 50 that contains (stores) the residual blood component obtained by removing the predetermined cells by the filter 40, a subsidiary or secondary bag (second bag) 52 that contains and preserves a supernatant component obtained by centrifuging the blood component of the primary bag 50, an additive solution bag (third bag) 54 that contains a red blood cell preservation liquid, and a delivery line 55 connected to the primary bag 50, the subsidiary bag 52, and the additive solution bag 54.

Similar to the blood collection bag 18, the primary bag 50, the subsidiary bag 52, and the additive solution bag 54 are formed in a bag shape by overlapping flexible sheet materials made of a flexible resin such as polyvinyl chloride or polyolefin and welding (through thermal fusion bonding or high-frequency fusion bonding) peripheral sealing portions of the sheet materials to each other.

The primary bag 50 serves as both a bag for containing (storing) the residual blood component obtained by removing the predetermined cells using the filter 40 and a bag for storing a precipitated component (concentrated red blood cells) obtained by centrifuging the residual blood component.

A branching connector (branching section) 62 is provided in the middle or intermediate portion of the delivery line 55 to connect the primary bag 50 and the subsidiary bag 52 and connect the primary bag 50 and the additive solution bag 54. In the example illustrated in the drawings, the delivery line 55 includes a first tube 56 connected to the primary bag 50, a second tube 58 connected to the subsidiary bag 52, a third tube 60 connected to the additive solution bag 54, the branching connector 62 connected to the first to third tubes 56, 58, and 60, and an openable/closable clamp 64 installed in the first tube 56.

A frangible part 66 is provided in one end (end in the primary bag 50 side) of the first tube 56 to prevent the blood component inside the primary bag 50 from transferring to other bags until the breaking operation. The frangible part 66 has the same configuration and functionality as those of the frangible part 32 described above.

The other end of the first tube 56 is connected to the first port 62a of the branching connector 62. One end of the second tube 58 is connected to the second port 62b of the branching connector 62. One end of the third tube 60 is connected to the third port 62c of the branching connector 62.

The clamp 64 is installed in the middle or intermediate portion of the first tube 56 and has a functionality of closing or opening a flow path of the first tube 56. A detailed configuration of the clamp 64 will be described later.

The red blood cell preservation liquid contained in the additive solution bag 54 may include a mannitol adenine phosphate (MAP) solution, a saline adenine glucose mannitol (SAGM) solution, OPTISOL, or the like. A frangible part 68 is provided in the end of the third tube 60 in the additive solution bag 54 side to prevent the red blood cell preservation liquid in the additive solution bag 54 from transferring to other bags. The frangible part 68 has the same configuration and functionality as those of the frangible part 32 described above.

Each tube of the blood bag system 10 is made of a transparent flexible resin. The clamps 30, 36 and 48 may be standard products that have been employed in other known systems. In addition, the clamps 30, 36, 48 and 64 are preferably classified depending on a place or a purpose of use. When the blood bag system 10 is sterilized or stored before use, the clamps 30, 36, 48 and 64 are unclamped, so that the bags internally communicate with each other to make a uniformly sterilized state.

Figure 2:
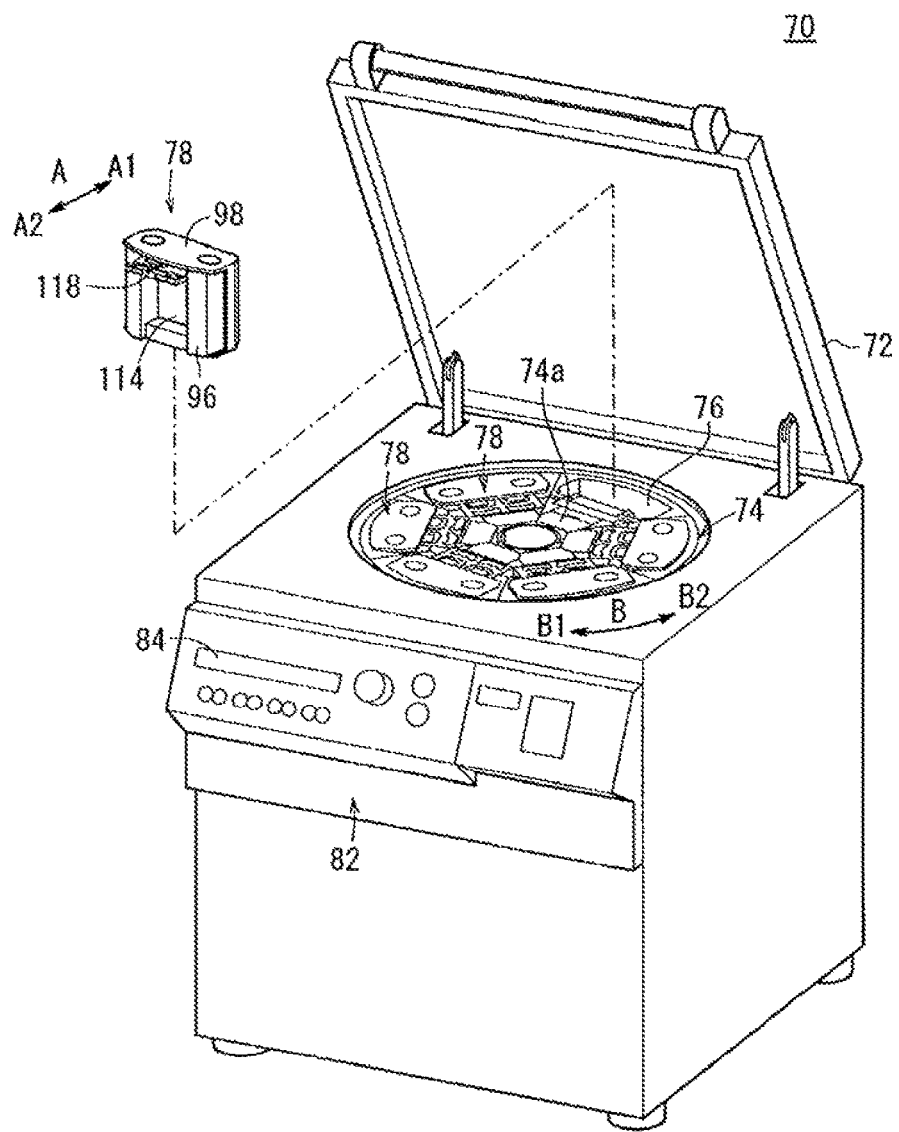
FIG. 2 is a perspective view of a centrifuge/delivery apparatus.

The blood bag system 10 according to the embodiment may be installed and used in a centrifuge/delivery apparatus 70 illustrated in FIG. 2. The centrifuge/delivery apparatus 70 is used to centrifuge the blood component contained in the primary bag 50 into two layers, including a plasma layer and a concentrated red blood cell layer, and deliver the plasma into the subsidiary bag 52 while the concentrated red blood cells remains in the primary bag 50.

For easy understanding of the method of using the blood bag system 10, a configuration of the centrifuge/delivery apparatus 70 will now be described. In addition, in the following description, it is assumed that the direction of arrow A in FIG. 2 indicates a radial direction, and the direction of arrow B indicates a circumferential direction. While the circumferential direction is strictly a direction along the circular arc as indicated by the arrow B, it is assumed that the direction orthogonal to arrow A is also referred to as the circumferential direction in the description thereof for convenience purposes.

As illustrated in FIG. 2, the centrifuge/delivery apparatus 70 has a box shape and includes: an openable/closable lid 72 on the upper surface; an internal centrifugal drum (centrifuging means) 74; six unit insertion holes 76 arranged inside the centrifugal drum 74 at a regular angular interval (60□); six insert units 78 inserted respectively into the unit insertion holes 76; and six pressers (pressing means) 80 (refer to FIG. 8) provided in a center retractably in a rotational radial direction with respect to each of the insert units 78. The centrifuge/delivery apparatus 70 is operated based on manipulation of a manipulation unit 82 provided in front and is controlled by a microcomputer to display predetermined information on a monitor 84.

Figure 3:
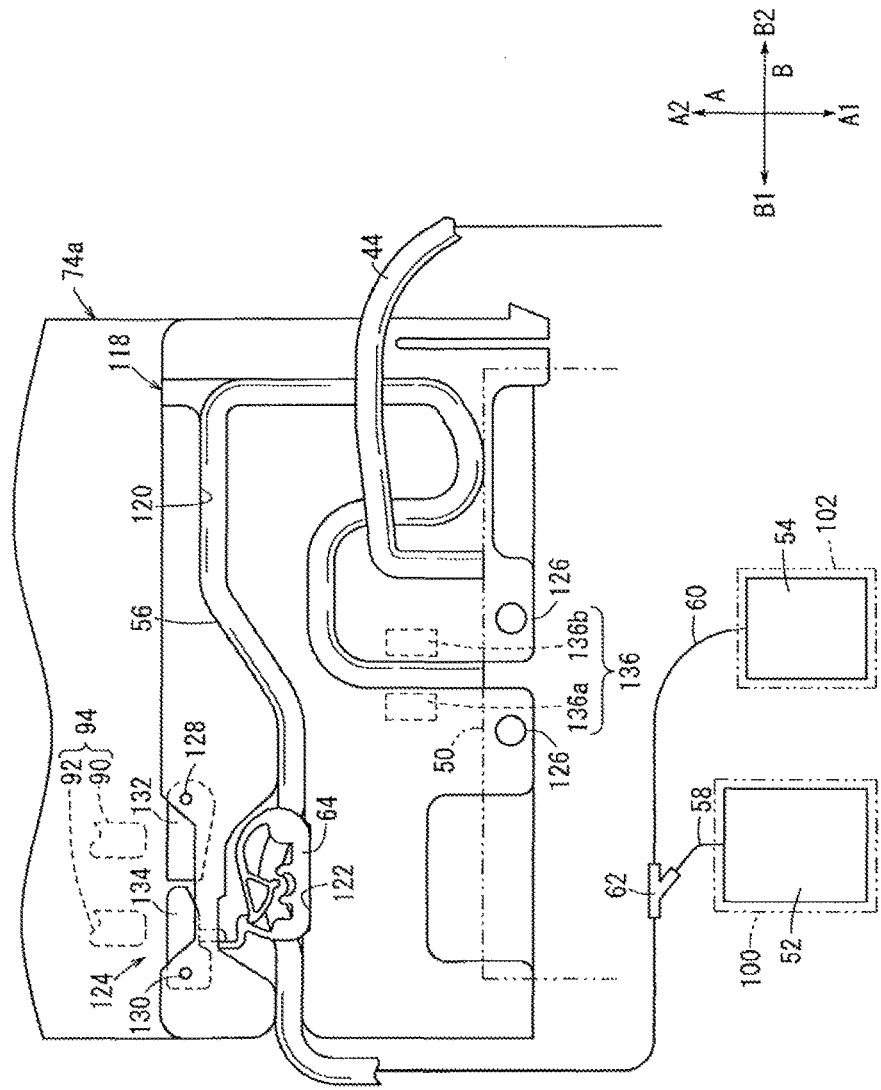
FIG. 3 is a schematic diagram illustrating a condition that a tube holder of the centrifuge/delivery apparatus holds a tube of the blood bag system.

As illustrated in FIG. 3, a central body 74a of the centrifugal drum 74 includes first and second rods 90 and 92 and the presser 80. The first and second rods 90 and 92 are driven to advance and retract in a radial direction A to serve as a clamp driving means 94 for clamping and unclamping the clamp 64.

As illustrated in FIG. 2, the insert unit 78 includes a unit body 96 and a cover body 98. The unit body 96 is a bottomed tube having a wide circular arc shape as seen in a plan view and is opened to the upper side. The unit body includes a first chamber 100 (refer to FIG. 3) having the subsidiary bag 52 housed therein, a second chamber 102 (refer to FIG. 3) having the additive solution bag 54 housed therein, and a third chamber 114 opened in the A2-direction where the primary bag 50 is housed.

The cover body 98 is installed in the unit body 96 from the outer face. Using the cover body 98, it is possible to cover an outer face, an upper face and a lower face of the unit body 96 and reliably hold the blood bag system 10 installed in the unit body 96.

The unit body 96 is provided at its upper portion with a plate-shaped tube holder 118 which projects toward the radially inner side. As illustrated in FIG. 3, the tube holder 118 has a tube guide passage 120 for guiding the first tube 56, and two pins 126, 126 provided at its end portion in the outward radial direction A1. The tube guide passage 120 is in the shape of a groove which is formed by walls on both sides of the groove which extend along roughly the whole length of the groove, and is open on the upper side.

The tube guide passage 120 extends in the inward radial direction A2 from the vicinity of the center of an end portion with respect to the outward radial direction A1 of the tube holder 118, is then bent in a reverse S pattern at an intermediate portion with respect to the radial direction A, and is bent in the vicinity of an end portion with respect to the inward radial direction A2 to extend in the B1 direction, until it reaches an end potion with respect to the B1 direction of the tube holder 118. The tube guide passage 120 is provided, at a portion forming a groove in the circumferential direction B, with a clamp holding section 122 for holding the above-mentioned clamp 64. The tube holder 118 further has a clamp manipulation section 124 for operating the clamp 64 into a closed state and an open state.

An upper portion of the primary bag 50 is fixed to the tube holder 118 by inserting a pair of pins 126 and 126 provided in the tube holder 118 into a pair of holes 50a, 50a (refer to FIG. 1) provided in the upper portion. The first tube 56 is installed and held in the tube guide passage 120 of the tube holder 118. In addition, the clamp 64 provided in the first tube 56 is held by the clamp holding section 122. The subsidiary bag 52 connected to the second tube 58 is housed in the first chamber 100. The additive solution bag 54 connected to the third tube 60 is housed in the second chamber 102.

Before the blood bag system 10 is installed in the centrifuge/delivery apparatus 70 after the residual blood component obtained by filtering whole blood using the filter 40 is delivered to and put in the primary bag 50, the outlet-side tube 44 is welded to prevent a leakage using a tube sealer or the like and is then cut out. Therefore, out of the blood bag system 10, only the separator unit 16 and a part of the outlet-side tube 44 are installed in the unit body 96.

The clamp 64 is manipulated or clamped/unclamped by the clamp manipulation unit 124 provided in the tube holder 118. The clamp manipulation unit 124 has a first pressing element 132 and a second pressing element 134 pivotably mounted with respect to the pins 128 and 130. The clamp 64 is clamped when the clamp 64 is pressed by the first pressing element 132. The clamp 64 is unclamped when the clamp 64 is pressed by the second pressing element 134. The clamping/unclamping manipulation or operation of the clamp 64 using the clamp manipulation unit 124 will be described in more detail below.

The tube holder 118 further has a sensor 136 that detects a type of the liquid passing through the first tube 56 at the upstream side of the clamp 64. The sensor 136 includes a light-transmitting section 136a and a light-receiving section 136b, and the type of the liquid can be determined based on a light transmission degree of the liquid passing between the light-transmitting section 136a and the light-receiving section 136b. A plurality of contacts electrically connected to the sensor 136 or an interface circuit of the sensor is provided on a lower surface of the tube holder 118. A signal from the sensor 136 can be supplied to the microcomputer by causing such contacts to make contact with the receive-side electrode provided in the central body 74a of the centrifugal drum 74.

The blood bag system 10 according to the present embodiment is basically configured as described above. The structure of the clamp 64 will next be described.

Figure 4:
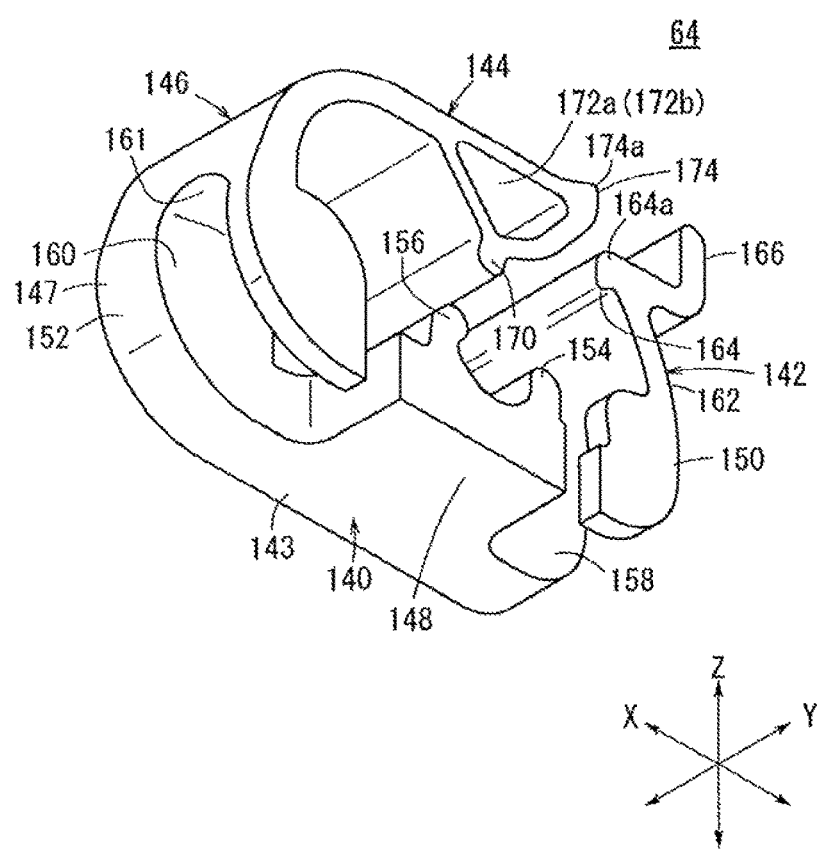
FIG. 4 is a perspective view of a clamp according to an embodiment disclosed by way of example here.
Figure 5:
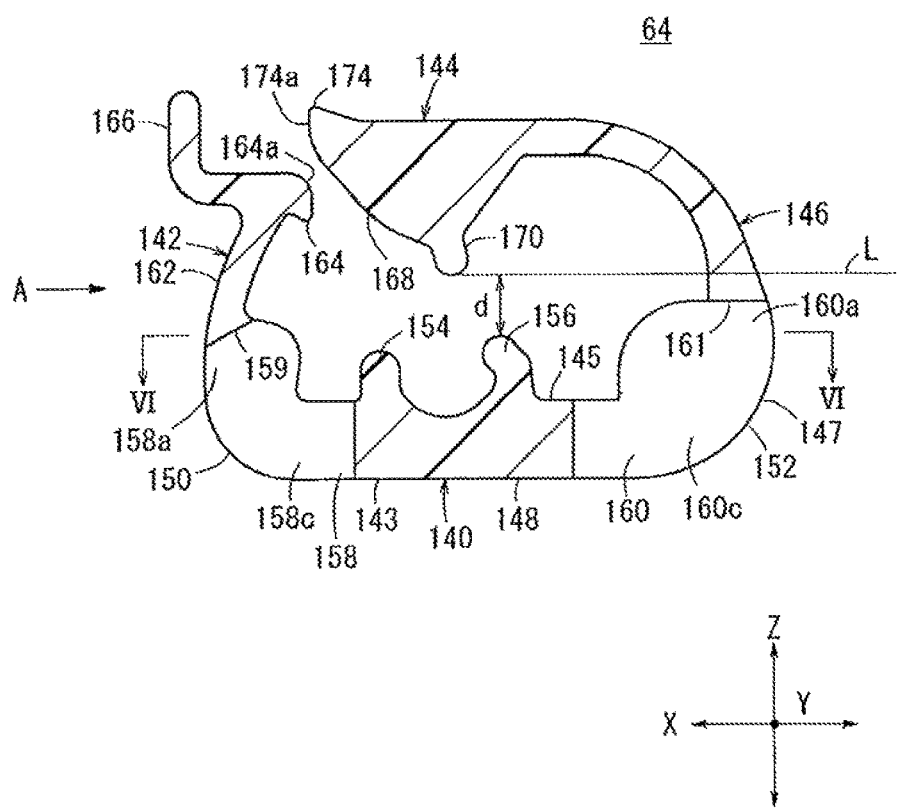
FIG. 5 is a longitudinal cross-sectional view of the clamp of FIG. 4.
Figure 6:
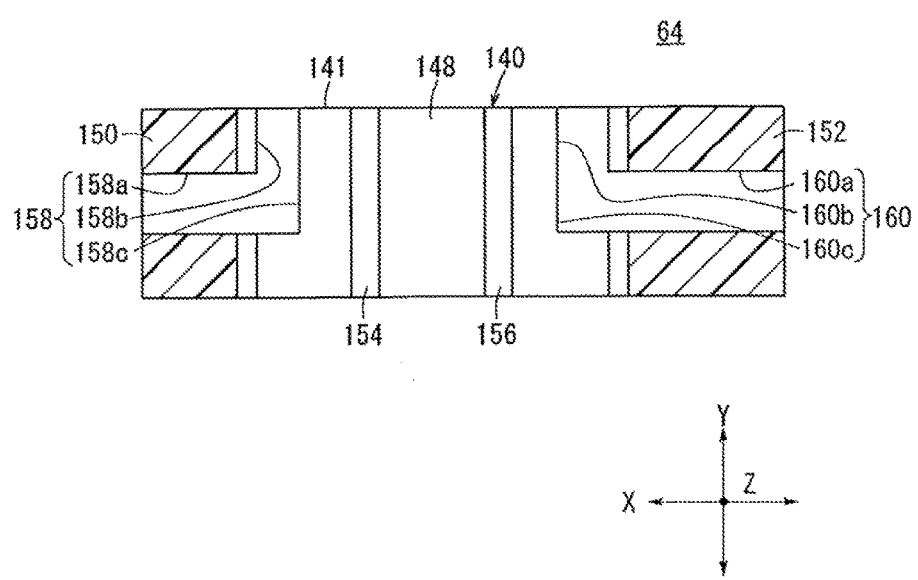
FIG. 6 is a cross-sectional view taken along the section line VI-VI of FIG. 5.

As illustrated in FIGS. 4 to 6, the clamp 64 is made of a resin material and includes a base section 140 formed in a substantially rectangular shape as seen in a plan view, a locking section 142 at one end of the base section 140, an opening/closing section 144 arranged to face the base section 140, and a bent section (intermediate section) 146 that connects the other end of the base section 140 and the opening/closing section 144. The opening/closing section 144 and the base section 140 are spaced apart from one another so that a space exists between the opening/closing section 144 and the base section 140. The base section 140, the locking section 142, the opening/closing section 144, and the bent section 146 are integrated into a single unitary, one-piece body.

In the following description of the clamp 64, an extending direction of the base section 140 is referred to as an X-direction, a width direction of the base section 140 perpendicular to the X-direction is referred to as a Y-direction, and a direction perpendicular to both the X-direction and the Y-direction is referred to as a Z-direction.

The base section 140 possesses a plate shape as a whole (i.e., is plate-shaped) and includes a relatively thin section (thinner section) 148 located in the center and relatively thick sections (thicker sections) 150 and 152 at both ends. On an inner surface (surface where the opening/closing section 142 is located) 145 of the thinner section 148, a protrusion section (third protrusion section) 154 and a protrusion section (first protrusion section) 156 are separated by a predetermined distance in the extending direction (X-direction). Each of the protrusion sections 154 and 156 extends across the entire width of the thin section 148 in the Y-direction.

As illustrated in FIG. 5, the protrusion section 154 extends from the base to the leading end substantially perpendicularly (Z-direction) to the inner surface 145 of the thinner section 148. The protrusion section 156 projects from the inner surface 145 of the thinner section 148 in a substantially perpendicular direction (Z-direction) and is slightly bent toward the locking section 142. In addition, a leading end of the protrusion section 156 is located slightly close to the opening/closing section 144 side relative to the leading end of the protrusion section 154.

In the base section 140, a pair of cutout sections 158 and 160 is formed along the extending direction (X-direction), and a pair of the protrusion sections 154 and 156 is interposed between the cutout sections 158, 160. The cutout section 158 includes a holding hole 158a penetrating the inner surface 145 and an outer surface 147 of one end side of the base section 140 to hold the first tube 56, a lateral through-hole 158b that penetrates the inner surface 145 and the bottom surface 143 of the base section 140 and is opened to one side surface 141 of the base section 140 to communicate with the first tube 56, and a communicating hole 158c communicating with the holding hole 158a and the lateral through-hole 158b. The side surface 141 intersects and extends away from the bottom surface 143.

That is, as illustrated in FIG. 6, the cutout section 158 is formed in a substantially L-shape (obtained by rotating the L-shape of FIG. 5 by 90°) as seen in a plan view and is opened to the bottom surface 143 and one side surface 141 of the base section 140.

Out of wall surfaces of the holding hole 158a, a surface (holding surface) 159 located in the locking section 142 side is inclined to the locking section 142 side along the inner surface 145 of the base section 140. In addition, while the clamp 64 is opened, a boundary between the holding surface 159 and the inner surface 145 is located in the opening/closing section 144 side relative to the protrusion section 156.

The cutout section 160 includes a holding hole 160a that penetrates the inner surface 145 and the outer surface 147 of the other end side of the base section 140 to hold the first tube 56, a lateral through-hole 160b that penetrates the inner surface 145 and the bottom surface 143 of the base section 140 and is opened to the one side surface 141 of the base section 140 to communicate with the first tube 56, and a communicating hole 160c communicating with the holding hole 160a and the lateral through-hole 160b.

That is, the cutout section 160 is formed in a substantially L-shape (horizontally reversed shape of the cutout section 158) as seen in a plan view and is opened to the bottom surface 143 and the one side surface 141 of the base section 140.

Out of the wall surfaces of the holding hole 160a, a surface (holding surface) 161 located in the bent section 146 side extends along the extending direction (X-direction) of the base section 140. In addition, in a released state of the clamp 64, the holding surface 161 is located in the opening/closing section 144 side relative to the protrusion section 156.

As illustrated in FIG. 5, the holding surface 159 of the cutout section 158 and the holding surface 161 of the cutout section 160 are located at the bottom surface 143 side of the base section 140 relative to a position (position of the line L) displaced from the leading end of the protrusion section 156 toward the opening/closing section 144 side by an outer diameter length d of the first tube 56. As a result, it is possible to securely bend a portion of the first tube 56 where the clamp 64 is installed (refer to FIG. 7A).

The locking section 142 includes an extending section 162 that extends from the thick section 150 to the opening/closing section 144 side, an engagement claw (engagement section) 164 provided at the leading end of the extending section 162 and engageable with the opening/closing section 144, and an engagement release section 166 integrally provided at one end of the engagement claw 164.

The engagement claw 164 extends across the entire width of the extending section 162 in the Y-direction and has a curved surface 164a located in a side opposite to the base section 140. The engagement release section 166 extends from one end of the engagement claw 164 to overhang or protrude outward and is bent to be distant from the base section 140 so that it can be engaged with the second pressing element 134 of the clamp manipulation unit 124.

The opening/closing section 144 possesses an overall plate shape and includes a swelling section 168 (swollen section or enlarged section) that has a triangular columnar shape and is swollen from an inner surface thereof to the base section 140 side and a pressing protrusion section (second protrusion section) 170 that is provided at the leading end of the swelling section 168 and presses a side surface of the first tube 56 toward the protrusion section 156.

In both side surfaces of the swelling section 168, triangular concave sections 172a and 172b are formed. In addition, a claw section 174 engageable with the engagement claw 164 is provided at one end of the swelling section 168. The claw section 174 extends across the entire width of the opening/closing section 144 in the Y-direction and has a curved surface 174a at the locking section 142 side. As illustrated in FIG. 4, the pressing protrusion section 170 is located at the protrusion section 154 side relative to the protrusion section 156 and projects toward the protrusion section 156. That is, the pressing protrusion section 170 is not located immediately above the protrusion section 156, but rather is shifted toward the protrusion section 154 side relative to the protrusion section 156.

In the clamp 64 according to the embodiment, it is preferable that a positional relationship between the pair of cutout sections 158 and 160 and the pair of protrusion sections 154 and 156, shapes, or the like (refer to FIG. 7A) be set such that a bent angle θ of the first tube 56 is set to 110° or greater and 150° or smaller while the side surface of the first tube 56 makes contact with the leading end of the protrusion section 156, the holding surface 159 of the cutout section 158, and the holding surface 161 of the cutout section 160.

If the bent angle θ is set to such a range, it is possible to appropriately suppress the flow path of the first tube 56 from being closed before the flow path of the first tube 56 is closed (in a pre-locked state). However, even when the bent angle θ of the first tube 56 is not in the aforementioned angle range, the flow path of the first tube 56 may not be closed in the pre-locked state depending on a diameter, a material, or the like of the first tube 56. Therefore, the bent angle θ may be set to any value.

Set forth next is a description of the operation and effects of the clamp 64 and the blood bag system 10 according to the present embodiment.

Figure 7A:
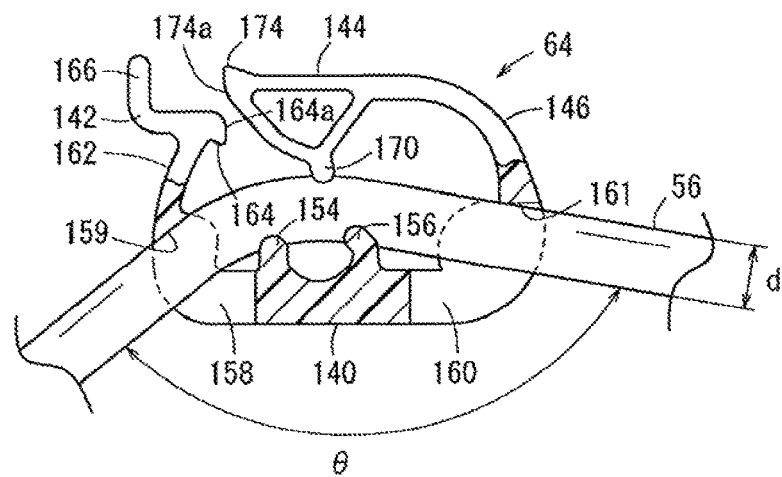
FIG. 7A is a front view illustrating a clamp in a pre-locking state.

First, as illustrated in FIG. 1 and FIG. 7A, the clamp 64 is installed or mounted at a predetermined position of the first tube 56 whose one end is connected to the primary bag 50 and whose other end is connected to the branching connector 62. Specifically, the first tube 56 is inserted into the holding hole 158a through the lateral through-hole 158b and the communicating hole 158c of the cutout section 158, and the first tube 56 is inserted into the holding hole 160a through the lateral through-hole 160b and the communicating hole 160c of the cutout section 160.

As a result, the first tube 56 makes contact with the holding surface 159 of the cutout section 158, the pair of protrusion sections 154 and 156, and the holding surface 161 of the cutout section 160. Therefore, the first tube 56 is bent at an obtuse angle.

In this state, since the first tube 56 is pressed against the holding surfaces 159 and 161 by virtue of its restoring force (elastic force), the clamp 64 does not easily move with respect to the first tube 56.

In this case, since the holding surface 159 is inclined to the opening/closing section 144 side along the inner surface 145 of the base section 140 as described above, the side surface of the first tube 56 makes contact with substantially the entire surface of the holding surface 159. As a result, it is possible to increase a frictional resistance by virtue of the contact between the holding surface 159 and the first tube 56. Therefore, the movement of the clamp 64 with respect to the first tube 56 is made more difficult.

As described above, since the bent angle θ of the first tube 56 is between 110° and 150°, the flow path of the first tube 56 is not closed in the pre-locked state.

Next, referring to FIG. 1, when blood is collected from a donor, first, the initial flow of blood collection is collected in the initial flow collecting bag 28 as described above. After the collection of the initial flow of blood collection is completed, the branching tube 34 is closed by the clamp 36, and the aforementioned breaking manipulation is performed for the frangible part 32 to open the flow path of the first blood collection tube 20. In this case, the clamp 30 is unclamped, whereas the frangible part 46 is set in the initial state (closed state). As a result, the blood from the donor flows through the second and first blood collection tubes 22 and 20 into the blood collection bag 18. After a predetermined amount of blood is collected and stored in the blood collection bag 18, the first blood collection tube 20 is closed by the clamp 30 so that the blood (whole blood) in the blood collection bag 18 does not flow out. In addition, the first blood collection tube 20 is welded and sealed by a tube sealer or the like, and the second blood collection tube 22 is then cut in the sealed portion.

Then, the blood collection bag 18 is disposed in an upper position, the primary bag 50 is disposed in a lower position, and the filter 40 is disposed in an intermediate position. Then, a breaking manipulation is performed for the frangible part 46 provided in one end of the inlet-side tube 42 to open the flow path in the inlet-side tube 42. As a result, the whole blood in the blood collection bag 18 flows through the inlet-side tube 42 into the filter 40, and leukocytes and platelets are removed in the course of passing through the filter 40, so that the residual blood component flows through the outlet-side tube 44 into the primary bag 50 and is stored therein. Then, the outlet-side tube 44 is welded and sealed in the downstream side of the clamp 48 using a tube sealer and the like, and the outlet-side tube 44 is cut in the sealed portion.

Then, in order to separate the blood component collected in the primary bag 50 into plasma and concentrated red blood cells and store the plasma and the concentrated red blood cells in predetermined bags, the separator unit 16 of the blood bag system 10 is installed in the centrifuge/delivery apparatus 70.

At the time of this installation, first, the flow path of the first tube 56 is closed by the clamp 64. Specifically, the outer surface of the opening/closing section 144 is pressed against or towards the base section 140 side with a finger by gripping the pre-locked clamp 64. Then, the curved surface 174a of the claw section 174 of the opening/closing section 144 makes contact with the curved surface 164a of the engagement claw 164 of the locking section 142.

As the outer surface of the opening/closing section 144 is further pressed, the bent section 146 is bent, and the curved surface 174a of the claw section 174 slides on the curved surface 164a of the engagement claw 164 and is displaced to the base section 140 side. Therefore, the locking section 142 (extending section 162) is slightly bent outward, and the side surface of the first tube 56 is pressed against the protrusion section 156 by the pressing protrusion section 170.

Figure 7B:
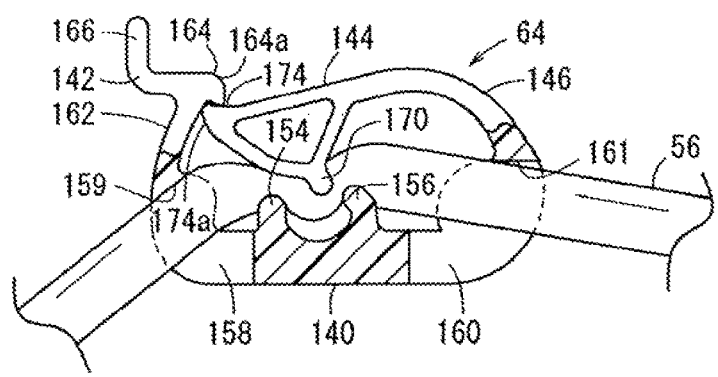
FIG. 7B is a front view illustrating a condition that a flow path of a first tube is closed by the clamp.

Then, after the curved surface 174a of the claw section 174 is released from the curved surface 164a of the engagement claw 164 (i.e., as the curved surface 174a of the claw section 174, moving towards the protrusion section 156 moves past the curved surface 164a of the engagement claw 164), a finger is released from the outer surface of the opening/closing section 144. As a result, the opening/closing section 144 is restored while the bent locking section 142 is restored. Therefore, the claw section 174 of the opening/closing section 144 is engaged with (abuts on) the engagement claw 164 of the locking section 142. As a result, the clamp 64 is closed, and the flow path of the first tube 56 is maintained in a closed state (refer to FIG. 7B).

In this case, as described above, the leading end of the protrusion section 156 is located slightly close to the opening/closing section 144 side relative to the leading end of the protrusion section 154. Therefore, it is possible to securely close the flow path of the first tube 56 using the protrusion section 156 and the pressing protrusion section 170, and the protrusion section 154 does not interfere. In addition, since the leading ends of each protrusion section 154, 156 and 170 are rounded, the side surface of the first tube 56 is not damaged.

When the flow path of the first tube 56 is closed, the aforementioned breaking manipulation is performed for the frangible part 66, and the flow path is opened. Then, as illustrated in FIG. 3, the first tube 56 is held by the tube holder 118, and the primary bag 50 is housed in the third chamber 114 of the unit body 96 (refer to FIG. 2) while an upper portion of the primary bag 50 is fixed to the tube holder 118. In this case, the clamp 64 is held by the clamp holding section 122 as illustrated in FIG. 3.

In addition, the subsidiary bag 52 is housed in the first chamber 100, and the additive solution bag 54 is housed in the second chamber 102. In this case, the subsidiary bag 52 is preferably housed in the first chamber 100 in a non-folded state in order to cause plasma to smoothly flow to and be stored in the subsidiary bag 52 in the separation process after the centrifuge process. As the separator unit 16 is installed and housed in the unit body 96, the cover body 98 is installed in the unit body 96 to assemble the insert unit 78.

Then, as illustrated in FIG. 2, the insert unit 78 that houses the blood bag system 10 is inserted into the unit insertion hole 76 of the centrifuge/delivery apparatus 70. As a result, a contact of the sensor or the interface circuit thereof makes contact with the electrode. While six insert units 78 are installed in the centrifuge/delivery apparatus 70 as illustrated, five or less insert units (preferably, three or two insert units arranged at a regular angular interval) may also be installed as long as the insert units are appropriately balanced.

Then, the lid 72 of the centrifuge/delivery apparatus 70 is closed, and the centrifuging process and the separating process are automatically performed by manipulating or operating the manipulation unit 82. In the automatic operation of the centrifuge/delivery apparatus 70, first, the centrifuging process is performed by rotating the centrifugal drum 74. In this case, as described above the clamp 64 is clamped. However, in order to reliably perform the process, it is preferable to close the clamp 64 as the first rod 90 advances once.

Figure 8:
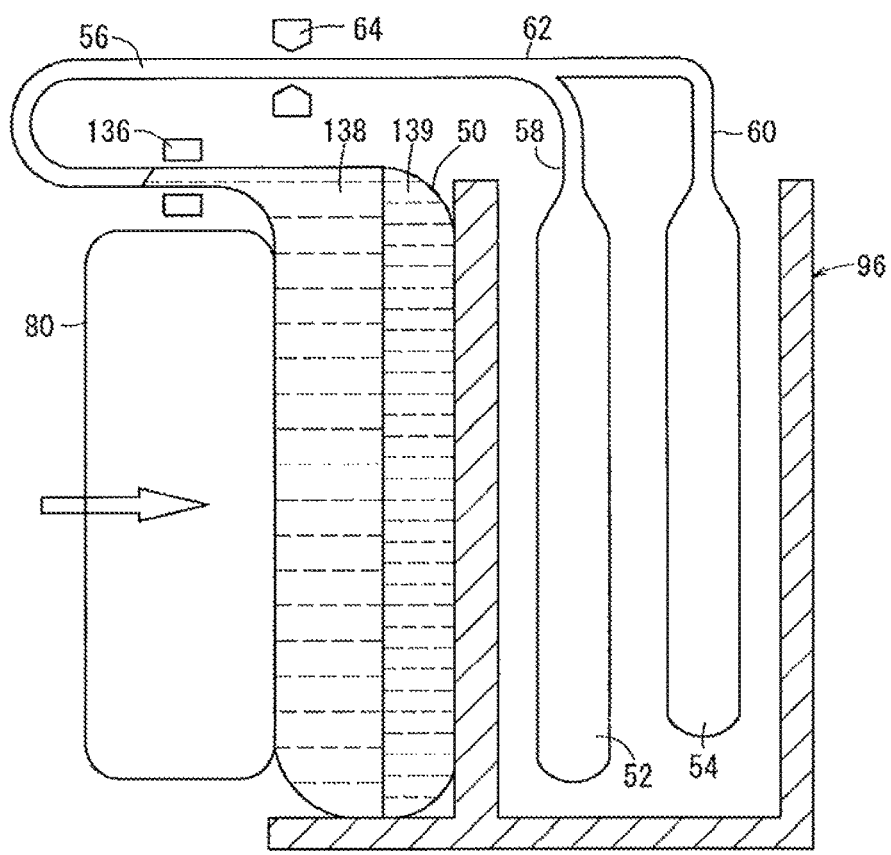
FIG. 8 is a diagram illustrating an action of the centrifuge/delivery apparatus.

As illustrated in FIG. 8, in the centrifuging process, the blood component stored in the primary bag 50 in the third chamber 114 receives a centrifugal force. As a result, the concentrated red blood cells 139 as a high specific gravity component are delivered in the outer diameter direction, whereas the plasma 138 as a low specific gravity component is delivered in the inner diameter direction, so that the blood component is separated into two layers.

The centrifuge/delivery apparatus 70 changes to the separating process after the centrifuging process. In the separating process, while rotation of the centrifugal drum 74 is maintained, the second rod 92 of the clamp driving means 94 is operated to open the flow path of the first tube 56.

Specifically, in the clamp 64 of FIG. 9A, the second rod 92 advances. Then, the second pressing element 134 is pivoted, and a release claw 134a provided in the second pressing element 134 is hooked on the engagement release section 166 of the clamp 64, so that the engagement release section 166 is displaced outward (in the B1-direction) (refer to FIG. 9B). Accordingly, the claw section 174 of the opening/closing section 144 is released from the engagement claw 164 of the locking section 142, and the engagement claw 164 is released. As a result, the opening/closing section 144 is restored (displaced in the A2-direction) as illustrated in FIG. 9C, so that the clamp 64 is released, and the flow path of the first tube 56 is opened. In addition, in this state, the second rod 92 is retracted to its original position.

Then, as illustrated in FIG. 8, the presser 80 is displaced in the centrifugal direction to press the primary bag 50. Since a volume of the primary bag 50 is reduced because it is clamped between the presser 80 and the wall, the liquid contained in the primary bag 50 is discharged from the first tube 56. In this case, since the first tube 56 is directed toward the inner diameter side, the plasma 138 located in the innermost diameter side flows from the primary bag 50 to the subsidiary bag 52 through the first tube 56, the branching connector 62, and the second tube 58.

After the plasma 138 flowing out of the primary bag 50 is completed, the concentrated red blood cells 139 start flowing from the primary bag 50. In this case, as the flow of the red blood cells through the first tube 56 is detected by the sensor 136 (refer to FIG. 3), the presser 80 is stopped, and the first rod 90 of the clamp driving means 94 is operated to close the flow path in the first tube 56 by the clamp 64. As a result, the red blood cells are inhibited from flowing to the subsidiary bag 52. The sensor 136 can detect the flow of the red blood cells through the first tube 56, based on the transparency (in other words, turbidity) of the liquid flowing through the first tube 56.

Figure 10A:
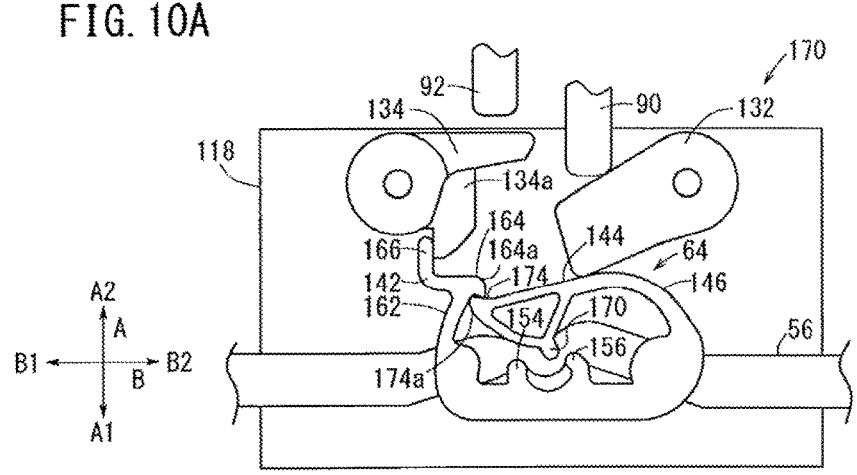
FIG. 10A is a diagram illustrating a condition that the engagement claw serving as a locking section is engaged with a claw section serving as an opening/closing section by pressing the opening/closing section.
Figure 10B:
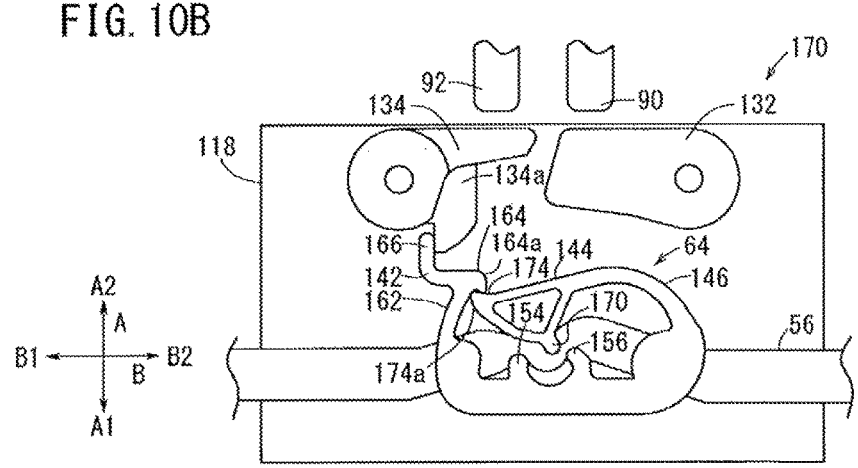
FIG. 10B is a diagram illustrating a condition that the tube is closed by pressing a pressing protrusion section.

Specifically, in the clamp 64 of FIG. 9C, the first rod 90 advances. Then, as illustrated in FIG. 10A, the first pressing element 132 is pivoted, and the opening/closing section 144 of the clamp 64 is pressed against the base section 140 side, so that the opening/closing section 144 is displaced in the A1-direction. As a result, the side surface of the first tube 56 is pressed toward the protrusion section 156 by the pressing protrusion section 170, and the claw section 174 of the opening/closing section 144 is engaged with the engagement claw 164 of the locking section 142. Therefore, the clamp 64 is closed, and the flow path of the first tube 56 is closed (refer to FIG. 10B). In addition, in this state, the first rod 90 is retracted to its original position.

In this manner, the flow path of the first tube 56 is closed to prohibit red blood cells from flowing to the subsidiary bag 52. In addition, the sensor 136 can detect that red blood cells flow through the first tube 56 based on transparency (in other words, turbidity) of the liquid flowing through the first tube 56.

As the separating process described above is terminated, the separator unit 16 is extracted from the insert unit 78, and the subsidiary bag 52 is removed by cutting the second tube 58 after the welding and sealing. Then, the additive solution bag 54 is disposed in an upper position, and the primary bag 50 is disposed in a lower position, and the flow path in the first tube 56 is opened by manipulating the clamp 64.

Specifically, the engagement release section 166 is pressed and displaced outward with a finger by gripping the closed clamp 64. Accordingly, the claw section 174 of the opening/closing section 144 is released from the engagement claw 164 of the locking section 142, and the engagement claw 164 is released. As a result, the opening/closing section 144 is restored. Therefore, the clamp 64 is released, and the flow path of the first tube 56 is opened (refer to FIG. 7A).

When the flow path of the first tube 56 is opened, the red blood cell preservation liquid in the additive solution bag 54 flows through the third tube 60 and the first tube 56 into the primary bag 50. When it is confirmed that the red blood cell preservation liquid is sufficiently discharged from the additive solution bag 54, the air is extracted from the primary bag 50, and the flow path of the first tube 56 is closed by manipulating the clamp 64. In this case, the manipulation of the clamp 64 is similar to that performed to close the clamp 64 with a finger as described above. Therefore, a detailed description is not repeated. In addition, the primary bag 50 is removed by cutting the first tube 56 after the welding and sealing.

Through the aforementioned process, it is possible to remove leukocytes and platelets from the whole blood, separate the residual blood component into two components including the plasma and the concentrated red blood cells, and separately put and preserve the plasma and the concentrated red blood cells in different bags (the primary bag 50 and the subsidiary bag 52).

In the clamp 64 according to the embodiment illustrated and described by way of example, each of the cutout sections 158 and 160 is opened to the bottom surface 143 and the side surface 141 of the base section 140. Therefore, it is possible to install the clamp 64 in the first tube 56 after one end of the first tube 56 is connected to the primary bag 50, and after the other end is connected to the branching connector 62.

As a result, it is possible to perform a process of installing the clamp 64 at any time in the manufacturing of the blood bag system 10. Therefore, it is possible to simplify manufacturing of the blood bag system 10. In addition, it is possible to relatively easily replace the clamp 64 even when a problem occurs in the clamp 64 after the blood bag system 10 is manufactured.

Since each of the cutout sections 158 and 160 is formed in a substantially L-shape as seen in a plan view, movement of the base section 140 in the first tube 56 in the width direction is restricted by the side surface of the base section 140 (thick sections 150 and 152) while the first tube 56 is inserted into each of the holding holes 158a and 160a. Therefore, it is rather difficult to detach the first tube 56 from a pair of the cutout sections 158 and 160.

In the clamp 64 according to the present embodiment, the protrusion section 156 and a pair of the cutout sections 158 and 160 are configured such that a portion (a portion making contact with the protrusion section 156 in the first tube 56) where the clamp 64 is installed in the first tube 56 is bent while the clamp 64 is released. As a result, the first tube 56 is pressed against the holding surface 159 of the cutout section 158 and the holding surface 161 of the cutout section 160 by virtue of its restoring force (elastic force). Therefore, it is possible to appropriately suppress movement of the clamp 64 with respect to the first tube 56.

Therefore, it is possible to suppress a location of the clamp 64 from being deviated or changed downward due to gravity when the red blood cell preservation liquid in the additive solution bag 54 flows into the primary bag 50 through the third tube 60 and the first tube 56, for example, while the additive solution bag 54 is located in an upper position, and the primary bag 50 is located in a lower position. Accordingly, it is possible to rather easily perform the clamping/unclamping manipulation of the clamp 64 at a predetermined position in the first tube 56.

In the clamp 64 according to the present embodiment, the holding surface 159 of the cutout section 158 and the holding surface 161 of the cutout section 160 are located in the pressing protrusion section 170 side relative to the leading end of the protrusion section 156 while the clamp 64 is released. Therefore, it is possible to bend the first tube 56 at an obtuse angle while the clamp 64 is installed in the first tube 56 (in a pre-locked state).

In the clamp 64 according to the present embodiment, the protrusion section 154 is formed between the protrusion section 156 and the cutout section 158 on the inner surface 145 of the base section 140 (thin section 148). Therefore, it is possible to further suppress the first tube 56 from being excessively bent (the bent angle θ of the first tube 56 is excessively reduced) and stably hold the first tube 56 in the pre-locked state of the clamp 64.

In the clamp 64 according to the present embodiment, the pressing protrusion section 170 is offset toward the protrusion section 154 side with respect to the protrusion section 156. Accordingly, compared to a case where the pressing protrusion section 170 and the protrusion section 156 are aligned in the extending direction of the base section 140, it is possible to increase a contact area of the inner surface of the first tube 56 when the first tube 56 is closed. Therefore, it is possible to securely close the flow path of the first tube 56.

The invention is not limited the aforementioned embodiment and variations, and it is natural that various modifications or changes are possible without departing from the scope and spirit of the invention.

For example, the clamp according may be applied to any flexible tube in addition to a tube of the blood bag system. That is, the clamp may apply to any tube capable of closing or opening the flow path.

The detailed description above describes a clamp and a blood bag system employing such a clamp which are disclosed by way of example. The invention is not limited, however, to the precise embodiment and variations described. Various changes, modifications and equivalents can be employed by one skilled in the art without departing from the spirit and scope of the invention as defined in the accompanying claims. It is expressly intended that all such changes, modifications and equivalents which fall within the scope of the claims are embraced by the claims.

What is claimed is:

1. A clamp positionable along a length of a flexible tube to close a flow path of the flexible tube when the clamp is in a closed position and to open the flow path of the flexible tube when the clamp is in a released position, the clamp comprising:

a base section possessing a bottom surface and an inner surface facing opposite directions, the base section also possessing side surfaces which intersect and extend away from the bottom surface, the base section including a first protrusion projecting from the inner surface to make contact with a side surface of the tube when the clamp is mounted on the tube;

an opening/closing section positioned in spaced apart and opposing relation to the base section so that a space exists between the opening/closing section and the base section, the opening/closing section including a second protrusion that projects toward the inner surface of the base section, the second protrusion being positioned to make contact with the flexible tube without closing the flow path of the tube when the clamp is in the released position and to make contact with the flexible tube and press the flexible tube toward the first protrusion to close off the flow path in the flexible tube when the clamp is in the closed position;

an intermediate section connecting the base section and the opening/closing section in a manner permitting the opening/closing section to move toward the base section when the clamp is in the released position;

the base section including first and second cutout sections through which the tube passes when the clamp is mounted on the tube, the first protrusion being positioned between the first and second cutout sections so that the first cutout section, the first protrusion and the second cutout section are arranged in order in an arrangement direction which is perpendicular to the side surfaces of the base section, the arrangement direction being an extending direction (X) of the base section;

the first protrusion and the first and second cutout sections being configured such that a portion of the tube passing through the clamp when the clamp is positioned along the tube is bent when the clamp is in the released position, wherein the side surface of the tube contacts the first protrusion section between the first and second cutout sections;

each of the first and second cutout sections being opened to one of the side surfaces of the base section located perpendicularly to the arrangement direction of the first and second cutout sections of the base section, and each of the first and second cutout sections having an opening on a planar portion of the bottom surface of the base section formed in a substantially L-shape as seen in a plan view from the bottom surface of the base section, wherein the first cutout section is at one end of the base section in the arrangement direction and the second cutout section is at an opposite end of the base section in the arrangement direction, and wherein a positional relationship of the first cutout section, the second cutout section, the first protrusion section, and the second protrusion section is such that the tube has an entry-to-exit angle from the first cutout section to the second cutout section in a pre-closed position between 110° and 150°; and wherein the base section, the intermediate section, and the opening/closing section are integrated into a single unitary, one-piece body.

2. The clamp according to claim 1, wherein the base section includes a third protrusion spaced from the first protrusion in the arrangement direction and projecting toward the opening/closing section to make contact with the flexible tube without closing the flow path of the tube when the clamp is in the released position.

3. The clamp according to claim 2, wherein the second protrusion is positioned between the first protrusion and the third protrusion in the arrangement direction.

4. The clamp according to claim 1, further comprising:
a locking section connected to one end of the base section, the locking section including a claw that engages a claw on the opening/closing section to lock the clamp in the closed position.

5. A clamp that closes a flow path of a flexible tube when the clamp is in a closed position and opens the flow path of the flexible tube when the clamp is in a released position, the clamp comprising:
a base section having a first protrusion section that makes contact with a side surface of the tube;
an opening/closing section having a second protrusion section that closes the flow path of the tube by pressing the side surface of the tube toward the first protrusion section;
an intermediate section connecting the base section and the opening/closing section;
the base section including a pair of cutout sections through which the tube is to pass, the first protrusion section being interposed between the pair of cutout sections;
the first protrusion section and the pair of cutout sections being configured such that a portion of the tube passing through the clamp when the clamp is installed on the tube is bent when the clamp is in the released position, wherein the side surface of the tube contacts the first protrusion section between the pair of cutout sections; and
wherein each of the pair of cutout sections is opened to a side surface of the base section located perpendicularly to an arrangement direction of the pair of cutout sections of the base section, which is an extending direction (X) of the base section, and wherein each of the pair of cutout sections has an opening on a planar portion of a bottom surface of the base section formed in a substantially L-shape as seen in a plan view from the bottom surface of the base section, wherein each of the pair of cutout sections comprises:
a holding hole that holds the tube, each of the holding holes penetrating the bottom surface of the base section and an inner surface of the base section;
a holding surface is located in an opening/closing section side of the holding hole of at least one of the cutout sections, the holding surface being located in a bottom surface side of the base section relative to a position displaced from a leading end of the first protrusion section toward the opening/closing section side by an outer diameter length of the tube; and
wherein a positional relationship of each of the holding holes, the first protrusion section, and the second protrusion section is such that the tube has an entry-to-exit angle from one of the pair of cutout sections to an other of the pair of the cutout sections in a pre-closed position between 110° and 150°.

6. The clamp according to claim 5, wherein the holding surface of at least one of the cutout sections is located on a side of the second protrusion section relative to the first protrusion section.

7. The clamp according to claim 5, wherein the holding surface of at least one of the cutout sections is inclined toward an opening/closing section side of the inner surface of the base section.

8. The clamp according to claim 5, wherein the base section is provided with a third protrusion section which is located between a first cutout section of the pair of cutout sections and the first protrusion section and which makes contact with the side surface of the tube.

9. A blood bag system comprising:
a plurality of bags each configured to contain whole blood or a blood component;
a flexible tube connecting the plurality of bags; and
a clamp according to claim 5, installed along the flexible tube.

10. A clamp positionable along a length of a flexible tube to close a flow path of the flexible tube when the clamp is in a closed position and to open the flow path of the flexible tube when the clamp is in a released position, the clamp comprising:
a base section possessing a bottom surface and an inner surface facing opposite directions, the base section also possessing side surfaces which intersect and extend away from the bottom surface, the base section including a first protrusion projecting from the inner surface to make contact with a side surface of the tube when the clamp is mounted on the tube;
an opening/closing section positioned in spaced apart and opposing relation to the base section so that a space exists between the opening/closing section and the base section, the opening/closing section including a second protrusion that projects toward the inner surface of the base section, the second protrusion being positioned to make contact with the flexible tube without closing the flow path of the tube when the clamp is in the released position and to make contact with the flexible tube and press the flexible tube toward the first protrusion to close off the flow path in the flexible tube when the clamp is in the closed position;
an intermediate section connecting the base section and the opening/closing section in a manner permitting the opening/closing section to move toward the base section when the clamp is in the released position;
the base section including first and second cutout sections through which the tube passes when the clamp is mounted on the tube, the first protrusion being positioned between the first and second cutout sections so that the first cutout section, the first protrusion and the second cutout section are arranged in order in an arrangement direction which is perpendicular to the side surfaces of the base section, the arrangement direction being an extending direction (X) of the base section;
the first protrusion and the first and second cutout sections being configured such that a portion of the tube passing through the clamp when the clamp is positioned along the tube is bent when the clamp is in the released position, wherein the side surface of the tube contacts the first protrusion between the first and second cutout sections; and each of the first and second cutout sections being opened to one of the side surfaces of the base section located perpendicularly to the arrangement direction of the first and the second cutout sections of the base section, and wherein the first and second cutout sections each have an opening on a planar portion of the bottom surface of the base section formed in a substantially L-shape as seen in a plan view from the bottom surface of the base section and the openings of the first and second cutout sections are at ends of the first and second cutout sections that are bottom-most ends, and which are opposite from a holding surface, the holding surface being located in a bottom surface side of the base section relative to a position displaced from a leading end of the first protrusion toward the opening/closing section by an outer diameter length of the tube, and wherein a positional relationship of the first cutout section, the second cutout section, the first protrusion, and the second protrusion is such that the tube is configured to extend about an entry axis.

11. The clamp according to claim 10, wherein the base section includes a third protrusion spaced from the first protrusion in the arrangement direction and projecting toward the opening/closing section to make contact with the flexible tube without closing the flow path of the tube when the clamp is in the released position.

12. The clamp according to claim 11, wherein the second protrusion is positioned between the first protrusion and the third protrusion in the arrangement direction.

13. The clamp according to claim 10, further comprising:
a locking section connected to one end of the base section, the locking section including a claw that engages a claw on the opening/closing section to lock the clamp in the closed position.

14. A blood bag system comprising:
a plurality of bags each configured to contain whole blood or a blood component;
a flexible tube connecting the plurality of bags; and
the clamp according to claim 10, installed along the flexible tube.

15. A method comprising:
mounting the clamp according to claim 10 on the flexible tube which possesses one end connected to a first bag and an opposite end connected to a second bag, the first and second bags each possessing an interior that receives blood or a blood component; and
the clamp being mounted on the tube at a position between the first bag connected to the one end of the tube and the second bag connected to the other end of the tube by passing a portion of the tube through the openings in the side surface of the base section and introducing the portion of the tube into the space between the base section and the opening/closing section.

16. The method according to claim 15, comprising:
introducing the portion of the tube into the space such that the first and second protrusions both contact the tube, the first and second protrusions contacting the side surface of the tube while a flow path through the tube remains open.

17. The method according to claim 16, wherein the clamp further comprises a locking section connected to one end of the base section, the method further comprising:
pushing the opening/closing section toward the base section to cause a claw on the opening/closing section to engage a claw on the locking section so that the clamp is in a closed position in which flow through the flow path in the tube is closed by virtue of the second protrusion pressing against the tube.

18. The method according to claim 15, wherein the clamp further comprises:
a locking section connected to one end of the base section, the method further comprising:
pushing the opening/closing section toward the base section to cause a claw on the opening/closing section to engage a claw on the locking section so that the clamp is in a closed position in which flow through a flow path in the tube is closed by virtue of the second protrusion pressing against the tube.

19. The method according to claim 15, wherein the first cutout section includes a first holding hole penetrating the inner surface and the bottom surface of the base section at one end side of the base section, the second cutout section including a second holding hole penetrating the inner surface and the bottom surface of the base section at an other end side of the base section, portions of the tube being held in the first and second holding holes.

* * * * *